United States Patent
Baxter et al.

(10) Patent No.: US 6,465,468 B1
(45) Date of Patent: Oct. 15, 2002

(54) HYDROXAMIC AND CARBOXYLIC ACID DERIVATIVES

(75) Inventors: Andrew Douglas Baxter; David Alan Owen; Duncan Batty; Robert John Watson, all of Cambridge (GB)

(73) Assignee: Darwin Discovery Limited (GB)

( * ) Notice: Subject to any disclaimer, the term of this patent is extended or adjusted under 35 U.S.C. 154(b) by 0 days.

(21) Appl. No.: 09/623,835

(22) PCT Filed: Mar. 22, 2000

(86) PCT No.: PCT/GB00/01076

§ 371 (c)(1),
(2), (4) Date: Sep. 8, 2000

(87) PCT Pub. No.: WO00/56704

PCT Pub. Date: Sep. 28, 2000

(30) Foreign Application Priority Data

Mar. 22, 1999 (GB) .............................................. 9906585
Nov. 24, 1999 (GB) .............................................. 9927782

(51) Int. Cl.⁷ ..................... C07C 311/13; C07D 295/26; C07D 211/96; A61K 31/16; A61K 31/445
(52) U.S. Cl. ............................ 514/252.12; 514/252.18; 514/309; 514/312; 514/331; 514/469; 514/575; 544/360; 544/383; 546/141; 546/153; 546/233; 546/234; 546/331; 549/467; 562/622; 562/623
(58) Field of Search ....................... 514/252.12, 252.18, 514/309, 312, 331, 469, 575; 544/360, 383; 546/141, 153, 233, 234, 331; 549/467; 562/622, 623

(56) References Cited

U.S. PATENT DOCUMENTS 3,992,441 A   11/1976   Helland .................. 262/518 A

FOREIGN PATENT DOCUMENTS

| EP | 1126672 | 9/1968 |
| GB | 1308022 | 2/1973 |
| WO | 9816503 | 4/1998 |
| WO | WO 98/38859 A1 * | 4/1998 |
| WO | 9838859 | 9/1998 |
| WO | WO 00/69819 A1 * | 11/2000 |

OTHER PUBLICATIONS

Andrews, C. H. et al. (1946) "Experimental Chemotherapy of Typhus. Anti–rickettsial Action of p–sulphonamidobenzamidine and Related Compounds" *Proceedings of the Royal Society of London* 133(133): 20–62.

Hoefle, M. L. et al. (1968) "Diuretics. 4–Substituted 3–Sulfamoylbenzoic Acid Hydrazides" *Journal of Medicinal Chemistry* 11(5):970–973.

Graafland, T. et al. (1979) "Structure and Reactivity in Intramolecular Catalysis. Catalysis of Sulfonamide Hydrolysis by the Neighboring Carboxyl Group" *Journal of the American Chemical Society* 101(23):6981–6991.

Reid, E. E. et al. (1955) "Some N–Alkylsaccharin Derivatives" *Journal of the American Chemical Society* 77(21):5628–5630.

Peet, N. P. et al. (1984) "Factors Which Influence the Formation of Oxadiazoles from Anthranihydrazides and Other Benzoylhydrazines" *Journal of Heterocyclic Chemistry* 21:1807–1816.

Israili, Z. H. et al. (1972) "Metabolites of Probenecid. Chemical, Physical, and Pharmacological Studies" *Journal of Medicinal Chemistry* 15(7):709–713.

Orazi, O. O. et al. (1986) "Intramolecular Sulphonyl–Amidomethylation. Part 1 [1,2]. Cyclization of Benzylsulphonamides" *Journal of Heterocyclic Chemistry* 23(6):1701–1708.

Sycheva, T. P. et al. (1955) "Synthesis of N–substituted 4–sulfamoylbenzoic Acids. I." *Chemical Abstracts* 49(2):1–25, XP–002129473 (abstract only).

* cited by examiner

*Primary Examiner*—Mukund J. Shah
*Assistant Examiner*—Thomas McKenzie
(74) *Attorney, Agent, or Firm*—Saliwanchik, Lloyd & Saliwanchik

(57) ABSTRACT

The subject invention concerns methods and compounds that have utility in the treatment of a condition associated with matrix metalloproteinase, ADAM or ADAM-TS enzymes, a condition that is mediated by TNF α or a condition involving a membrane-shedding event that is mediated by a metalloproteinase. Compounds of the invention are of formula I

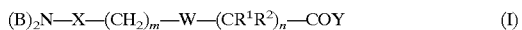

$$(B)_2N-X-(CH_2)_m-W-(CR^1R^2)_n-COY \quad (I)$$

wherein n=0 or 1;

m=0 or 1;

X is $S(O)_{1-2}$;

Y is OH or NHOH;

W is aryl or heteroaryl;

and the other groups are as defined herein.

14 Claims, No Drawings

HYDROXAMIC AND CARBOXYLIC ACID DERIVATIVES

FIELD OF THE INVENTION

This invention relates to hydroxamic and carboxylic acid derivatives, and to their use in medicine.

BACKGROUND OF THE INVENTION

Metalloproteinases, including matrix metalloproteinase (MMP), (human fibroblast) collagenase, gelatinase and TNFα convertase (TACE), and their modes of action, and also inhibitors thereof and their clinical effects, are described in WO-A-96/11209, WO-A-97/12902 and WO-A-97/19075, the contents of which are incorporated herein by reference. MMP inhibitors may also be useful in the inhibition of other mammalian metalloproteinases such as the ADAM or ADAM-TS families. Members of the ADAM family include TNFα convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNFα both in vitro and in vivo. See Gearing et al (1994), Nature 370:555–557; McGeehan et al (1994), Nature 370:558–561; GB-A-2268934; and WO-A-93/20047. All of these reported inhibitors contain a hydroxamic acid zinc-binding group, as do the imidazole-substituted compounds disclosed in WO-A-95/23790. Other compounds that inhibit MMP and/or TNFα are described in WO-A-95/13289, WO-A-96/11209, WO-A-96/035687, WO-A-96/035711, WO-A-96/035712 and WO-A-96/03 5714.

WO-A-98/38859 discloses sulfonyl-divalent aryl/heteroaryl hydroxamic compounds as MMP inhibitors. In addition to the claimed compounds, it discloses related compounds including N-hydroxy-2-[[4-(phenylmethyl)-1-piperidinyl]sulfonyl]benzamide, as having inferior properties.

Probenecid, i.e. 4-[(dipropylamino)sulfonyl]benzoic acid, has long been known as a uricosuric agent; see U.S. Pat. No. 2,608,507. Certain metabolites are reported by Israeli et al, J. Med. Chem. 15(7):709–13 (1972).

SUMMARY OF THE INVENTION

The invention encompasses novel compounds of formula (I) which are useful ihibitors of matrix metalloproteinase, ADAM or ADAMTS enzymes, and which are useful for the treatment of diseases mediated by those enzymes and/or TNFα mediated diseases, including degenerative diseases and certain cancers.

Novel compounds according to the invention are of the general type represented by formula (1):

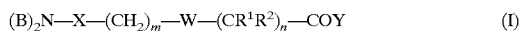  (I)

(B)$_2$N—X—(CH$_2$)$_m$—W—(CR$^1$R$^2$)$_n$—COY wherein n=0–1;

m=0–1;

X is S(O)$_{1-2}$;

Y is OH or NHOH;

W is aryl or heteroaryl;

R$^1$ is H, OR$^7$ or a group (optionally substituted with R$^3$) selected from C$_{1-6}$ alkyl, C$_{2-6}$ alkenyl, C$_{2-6}$ alkynyl, aryl, C$_{1-6}$ alkyl-aryl, heteroaryl, C$_{1-6}$ allyl-heteroaryl, cycloalkyl, C$_{1-6}$ alkyl-cycloalkyl, heterocycloalkyl, C$_{1-6}$ alkyl-heterocycloalkyl; and R$^2$ is H or C$_{1-6}$ alkyl;

or CR$^1$R$^2$ is cycloalkyl or heterocycloalkyl optionally substituted with R$^3$ or a group (optionally substituted with R$^3$) selected from C$_{1-6}$ alkyl, aryl, C$_{1-6}$ alkyl-aryl, heteroaryl, C$_{1-6}$; alkyl-heteroaryl;

R$^3$ is OR$^7$, COR$^7$, CO$_2$R$^8$, CON(R$^7$)$_2$, N(R$^7$)$_2$, NR$^7$COR$^7$, NR$^7$CON(R$^7$)$_2$, NR$^7$CO$_2$R$^8$, NR$^7$SO$_2$R$^8$, S(O)$_{0-2}$R$^8$, SO$_2$N(R$^7$)$_2$ or cycloimidyl (optionally substituted with R$^4$);

R$^4$ is C$_{1-6}$ alkyl;

B is H or a group (optionally substituted with R$^5$ or R$^6$) selected from C$_{1-6}$ alkyl, C$_{2-6}$ alkenyl, C$_{2-6}$ alkynyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl, C$_{1-6}$ alkyl-heterocycloalkyl, cycloalkenyl, and heterocycloalkenyl; and each instance of B may be the same or different;

R$^5$ is a group (optionally substituted with R$^6$) selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl and C$_{1-6}$ alkyl-heterocycloalkyl;

or B—N—B is heterocycloalkyl optionally substituted with R$^5$, R$^6$, =O or =NOR$^5$;

R$^6$ is a group selected from N(R$^7$)$_2$, NR$^7$COR$^7$, NR$^7$CON(R$^7$)$_2$, NR$^7$CO$_2$R$^8$, NR$^7$SO$_2$R$^8$, OR$^7$, COR$^7$, CO$_2$R$^4$, CON(R$^7$)$_2$S(O)$_{0-2}$R$^8$, and SO$_2$N(R$^7$)$_2$;

R$^7$ is H or a group selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl and C$_{1-6}$ alkyl-heterocycloalkyl, wherein said group is optionally substituted with R$^8$, COR$^8$, SO$_{0-2}$R$^8$, CO$_2$R$^8$, OR$^8$, CONR$^4$R$^8$, NR$^4$R$^8$, or SO$_2$NR$^4$R$^8$ and for each case of N(R$^7$)$_2$ the R$^7$ groups are the same or different or N(R$^7$)$_2$ is heterocycloalkyl optionally substituted with R$^8$, COR$^8$, SO$_{0-2}$R$^8$, CO$_2$R$^8$, OR$^8$, CONR$^4$R$^8$, NR$^4$R$^8$, or SO$_2$NR$^4$R$^8$;

R$^8$ is C$_{1-6}$ alkyl, aryl, C$_{1-6}$ alkyl-aryl, heteroaryl or C$_{1-6}$ alkyl-heteroaryl; and the salts, solvates, hydrates, N-oxides, protected amino, protected carboxy and protected hydroxamic acid derivatives thereof Many compounds of formula I are new.

DESCRIPTION OF THE INVENTION

Preferred compounds of the invention are those wherein X is SO$_2$; Y is NHOH and/or B—N—B is optionally substituted heterocycloalkyl. Other preferences are defined in the subclaims.

It will be appreciated that the compounds according to the invention can contain one or more asymmetrically substituted carbon atoms. The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

It will further be appreciated that the compounds according to the invention may contain an oxime. This oxime can give rise to geometrical isomers, and in each case the invention is to be understood to extend to all such isomers and mixtures thereof.

As used in this specification, alone or in combination, the term "$C_{1-6}$ alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "$C_{2-6}$ alkynyl" refers to a straight or branched chain alkyl moiety having two to six carbon atoms and having in addition one triple bond. This term would include for example, ethynyl, 1-propynyl, 1- and 2-butynyl, 1-methyl-2-butynyl etc.

The term "cycloalkyl" refers to a saturated alicyclic moiety having from three to eight, e.g. 3–6, carbon atoms and includes, for example, cyclopropyl, cyclobutyl, cyclopentyl, cyclohexyl, cycloheptyl, cyclooctyl and bicyclo[2.2.1]heptanyl.

The term "cycloalkenyl" refers to an alicyclic moiety having from three to eight carbon atoms and having in addition one double bond. This term includes, for example, cyclopentenyl, cyclooctenyl and bicyclo[2.2.1]heptenyl.

The term "heterocycloalkyl" refers to a saturated heterocyclic moiety having from two to eight, e.g. 2–6, carbon atoms and one or more heteroatom from the group N, O, S (or oxidised versions thereof) which may be optionally benzofused at any available position. This includes, for example, azetidinyl, pyrrolidinyl, tetrahydrofuranyl, piperidinyl, benzodioxole and 8-oxabicyclo[3.2.1]octane.

The term "heterocycloalkenyl" refers to an alicyclic moiety having from three to eight carbon atoms and one or more heteroatoms selected from N, O, S and oxidised versions thereof, and having in addition one double bond. This term includes, for example, dihydropyranyl and 8-oxabicyclo[3.2.1]octene.

The term "aryl" refers to an aromatic carbocyclic radical having a single ring or two condensed rings, optionally substituted with an aryl group substituent. This term includes, for example, phenyl and naphthyl.

The term "heteroaryl" refers to aromatic ring systems of five to ten atoms of which at least one atom is selected from O, N and S, and optionally substituted with an aryl group substituent. This term includes, for example, furanyl, thiophenyl, pyridyl, indolyl and quinolyl.

The term "aryl group substituent" refers to a substituent chosen from halogen, CN, $CF_3$, $CHF_2$, $CH_2F$, $OCF_3$, $OCHF_2$, $OCH_2F$ and $NO_2$. The substituent may also be $OC_{1-6}$ alkyl.

The term "halogen" means fluorine, chlorine, bromine or iodine.

The term "benzofused" refers to the addition of a benzene ring sharing a common bond with the defined ring system.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "optionally substituted" means optionally susbstituted with one or more of the groups specified, at any available position or positions.

The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substitued derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^9$ where $R^9$ may be an ethyl, benzyl, phenethyl, phenylpropyl, α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes.

It will be appreciated that, where a particular stereoisomer of formula (I) is required, the synthetic processes described herein may be used with the appropriate homochiral starting material and/or isomers maybe resolved from mixtures using conventional separation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, W, B, X and Y are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene et al, "Protective Groups in Organic Synthesis", Wiley Interscience.

A process for preparing compounds of general formula (I) comprises acylating an amine of formula $B_2NH$ (II) with an acylating agent of formula Z—X—$(CH_2)_m$—W—$(CR^1R^2)_n$—COY (III) wherein Z represents a suitable leaving group (e.g. a halogen such as chlorine), and Y is OH or NHOH or protected forms thereof such as $OR^{10}$ (where $R^{10}$ is a suitable protecting group such as benzyl or tert-butyl) or $NHOR^{11}$ (where $R^{11}$ is a suitable protecting group such as benzyl, tert-butyl or tert-butyldimethylsilyl).

Acylating agents of formula (III) where m=0 and X is $SO_2$, if not available commercially, may be prepared in a two-step process involving the sulfonation of an aromatic group of formula W—$(CR^1R^2)_n$—COY (IV) to give a sulfonic acid HO—$SO_2$—W—$(CR^1R^2)_n$—COY (V) followed by activation to (III). Many compounds of formula (IV) are available, or may be prepared by methods known to those skilled in the art.

Acylating agents of formula (III) where m=1 and X is $SO_2$ may be prepared from compounds of formula $R^{12}S—CH_2—W—(CR^1R^2)_n—COY$ (VI), where $R^{12}$ is H or a suitable labile group such as acetyl, by treatment with chlorine in an appropriate solvent such as water at an appropriate temperature such as 0° C. Acylating agents of formula (III) where X=SO may be prepared from compound (VI) by treatment with $SO_2Cl_2$ and acetic anhydride in an appropriate solvent such as dichloromethane at an appropriate temperature such as 0° C.

Sulfanyl compounds of formula (VI) may be prepared readily by alkylation of a compound $R^{12}SH$ with an alkylating agent of the form $Z^A—CH_2—W—(CR^1R^2)_n—COY$ (VII), where $Z^A$ is a leaving group (e.g. a halogen such as bromine, or an alkylsulfonate ester such as methanesulfonate). Many compounds of the form (VII) are available commercially, or may be prepared by standard chemistry known to those skilled in the art from materials available commercially.

Amines of the structure depicted in formula (II) are commercially available or may be prepared by standard aromatic, heteroaromatic or other chemistry known to those skilled in the art, from commercially available materials.

Compounds of formula (I) may also be prepared by interconversion of other compounds of formula (I). Thus, for example, compound of formula (I) where $X=SO_2$ may be prepared from a compound of formula (I) where X=SO by oxidation with, for example sodium periodate and ruthenium chloride trihydrate in an appropriate solvent, for example acetonitrile-tetrachloromethane-water. Hydroxamic acids (Y=NHOH) of general formula (I) may be prepared from carboxylic acids (Y=OH) of formula (I) using methods known to those skilled in the art.

Similarly, intermediates of any appropriate formula may be prepared by the interconversion of other compounds of the same formula. Thus, for example, a compound of formula (VI) where $R^2$ is not H may be prepared from a compound of formula (VI) where $R^2$ is H by reaction with a compound $R^2Z$ (where Z is as defined above) in the presence of a strong base such as lithium diisopropylamide in an inert solvent such as tetrahydrofuran.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysin, collagenase, gelatinase, ADAM or ADAM-TS enzymes. Compounds according to the invention may also exhibit in vitro inhibition of membrane-shedding events known to be mediated by metalloproteinases, for example, α-APP, ACE, TGF-α, TNF-α, Fas ligand, selecting, TNFR-I, TNFR-II, CD30, II-6R, CD43, CD44, CD16-I, CD16-II, Folate receptor, CD23, or IL-1RII.

The activity and selectivity of the compounds may be determined by use of the appropriate enzyme inhibition test, for example as described in Examples A–M of WO-A-98/05635, by the assay for the inhibition of CD23 shedding described in WO-A-99/24399, or by the following assay of TNF RI shedding.

The potency of the compounds of general formula (I) to act as inhibitors of the production of TNF RI is determined using the following procedure. A 100 μM solution of the inhibitor being tested or dilutions thereof is incubated at 37° C. in an atmosphere of 5% $CO_2$ with peripheral blood mononuclear cells (PBMC). PBMC are isolated from buffy coats by standard procedures using Ficoll. A 100 μM solution of the inhibitor being tested or dilutions thereof is incubated for 22 hours at 37° C. in an atmosphere of 5% $CO_2$ with 1×10$^6$/ml PBMC stimulated with LPS. The cells are centrifuged down and the supernatant is assayed for TNF RI using a commercially available ELISA kit (R & D Systems). The activity in the presence of 0.1 mM inhibitor or dilutions thereof is compared to activity in a control devoid of inhibitor and results reported as that inhibitor concentration effecting 50% inhibition of the production of TNF RI.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases, cancer, cardiovascular diseases, diseases involving tissue breakdown such as rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis and aspirin-independent anti-thrombosis.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouthwashes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate compounds of the invention.

INTERMEDIATE 1

4-(4-Hydroxyphenyl)piperazine-1-carboxylic acid tert-butyl ester

To a stirred solution of 1-(4-hydroxyphenyl)piperazine (25 g) in dichloromethane (150 ml) at 0° C. was added a solution of di-tert-butyl dicarbonate (36.7 g) in dichloromethane (50 ml) dropwise. Stirring was continued for 30 mins at this temperature and then stirred at RT for a further 24 h. The reaction mixture was washed with 10% aqueous citric acid (3×50 ml), saturated aqueous sodium hydrogen carbonate solution (3×50 ml), water (3×50 ml) and brine (50 ml). The organic layer was then dried ($Na_2SO_4$), filtered and the solvent removed under reduced pressure to give the title compound (33.9 g, 87%) as a brown solid.

$R_f$ 0.13 (1:1 diethyl ether/hexane);
MS 278 ($M^+$).

INTERMEDIATE 2

4-(4-Difluoromethoxyphenyl)piperazine-1-carboxylic acid tert-butyl ester

To a stirred solution of Intermediate 1 (2.0 g) in 1,4-dioxan (50 ml) at 100° C. was added a solution of sodium hydroxide (0.86 g) in water (5 ml). Through this mixture was bubbled chlorodifluoromethane for 15 mins at this temperature before being allowed to cool to RT. The solvent was removed under reduced pressure and resulting residue was partitioned between diethyl ether (100 ml) and water (50 ml). The organic layer collected and further washed with saturated aqueous sodium hydrogencarbonate solution (3×50 ml), water (3×50 ml) and brine (50 ml). The organic layer was then dried ($Na_2SO_4$), filtered and the solvent removed under reduced pressure to give the title compound (1.44 g, 61%) as a beige solid.

$R_f$ 0.51 (1:1 diethyl ether/hexane);
MS 329 ($MH^+$).

INTERMEDIATE 3

1-(4-Difluoromethoxyphenyl)piperazine dihydrochloride

To a stirred solution of Intermediate 2 (1.4 g) in dichloromethane (10 ml) at 0° C. was added a solution of trifluoroacetic acid (5 ml) in dichloromethane (5 ml). Stirring was continued for 30 mins at this temperature and then stirred at RT for a further 2 h. The solvent was removed under reduced pressure and the resulting residue azeotroped with 1:1 hexane/dichloromethane (3×20 ml). Treatment of this material with a solution of hydrogen chloride in diethyl ether (1.0M, 20 ml) gave a suspension, which was subsequently collected by filtration. The precipitation was washed further with diethyl ether (3×20 ml) and dried under reduced pressure to give the title compound (0.74 g, 76%).

$R_f$ 0.15 (ethyl acetate);
MS 229 ($MH^{3O}$).

INTERMEDIATE 4

2-(Bromomethyl)benzoic acid methyl ester

Prepared as described by Dhanoa, *J. Med. Chem.*, 36, 4230, (1993).

$R_f$ 0.44 (5:1 hexane/diethyl ether);
MS 229 ($M^+$).

INTERMEDIATE 5

2-(Cyanomethyl)benzenesulfonyl chloride

Prepared as described by Sianesi et al, *Chem. Ber.*, 103, 1992–2002, (1970).

$R_f$ 0.60 (1:1 hexane/ethyl acetate);
MS 216 ($M^+$).

INTERMEDIATE 6

(3a,7a-Dihydrobenzofuran-2-ylmethyl)methylamine

To a stirred solution of benzofuran-2-carboxaldehyde (1.50 g) and 4 Å molecular sieves in dichloroethane (50 ml) under an atmosphere of nitrogen was added methylamine in THF (2.0M, 10.3 ml) and acetic acid (1.23 g). Stirring was continued for 2 h before sodium triacetoxyborohydride (2.18 g) was added and stirring as continued overnight. The mixture was filtered, absorbed onto silica gel and chromatographed eluting with dichloromethane/methanol (9:1) to yield the title compound (1.05 g, 64%) as an off-white solid.

$R_f$ 0.30 (9:1 dichloromethane/methanol);
MS 229 ($M^+$).

INTERMEDIATE 7

2-[4-(4-Chlorophenyl)piperazine-1-sulfonyl]benzoic acid methyl ester

To stirred suspension of 4-(4-chlorophenyl)piperazine dihydrochloride (3.0 g) in dichloromethane (100 ml) at 0° C. was added triethylamine (4.6 ml). After 15 mins, a solution of 2-chlorosulfonylbenzoic acid methyl ester (2.90 g) in dichloromethane (30 ml) was added. Stirring was continued overnight with the temperature rising to RT. The reaction mixture was diluted with dichloromethane (100 ml) and then washed with 10% aqueous citric acid (3×50 ml), saturated aqueous sodium hydrogen carbonate solution (3×50 ml), water (3×50 ml) and brine (50 ml). The organic layer was then dried ($MgSO_4$), filtered and the solvent removed under reduced pressure to give the title compound (0.24 g, 48%) as an off-white solid.

$R_f$ 0.57 (1:1 hexane/ethyl acetate);
MS 395 ($MH^+$).

Similarly prepared were:

INTERMEDIATE 8

2-[4-(4-Chlorophenoxy)piperidine-1-sulfonyl] benzoic acid methyl ester

From 2-chlorosulfonylbenzoic acid methyl ester (587 mg) and 4-(4-chlorophenoxypiperidine (577 mg) as a brown oil (0.83 g, 97%).

$R_f$ 0.53 (1:1 diethyl ether/hexane);
MS 410.6 (MH$^+$).

INTERMEDIATE 9

2-[4-(4-Difluoromethoxyphenyl)piperazine-1-sulfonyl]benzoic acid methyl ester

From 2-chlorosulfonylbenzoic acid methyl ester (587 mg) and Intermediate 3 (602 mg) as a brown oil, (0.85 g, 99%).

$R_f$ 0.44 (1:1 diethyl ether/hexane);
MS 426 (M$^+$).

INTERMEDIATE 10

2-[4-(3,5-Dichlorophenyl)piperazine-1-sulfonyl] benzoic acid methyl ester

From 2-chlorosulfonylbenzoic acid methyl ester (587 mg) and 4-(3,5-dichlorophenyl)piperazine (462 mg) as a green solid (0.76 g, 89%).

$R_f$ 0.58 (1:1 diethyl ether/hexane);
MS 429 (M$^+$).

INTERMEDIATE 11

2-[4-(4-Trifluoromethylpyridin-2-yl)piperazine-1-sulfonyl]benzoic acid methyl ester From 2-chlorosulfonylbenzoic acid methyl ester (587 mg) and 4-(4-trifluoromethylpyridin-2-yl)piperidine (462 mg) as a brown oil (0.83 g, 96%).

$R_f$ 0.62 (ethyl acetate);
MS 429 (M$^+$).

INTERMEDIATE 12

2-[4-(4-Chlorobenzoyl)piperidine-1-sulfonyl] benzoic acid methyl ester

From 2-chlorosulfonylbenzoic acid methyl ester (0.25 g) and 4-(4-chlorobenzoyl)piperidine (221 mg) as a yellow oil (0.28 g, 78%).

$R_f$ 0.55 (1:1 diethyl ether/hexane);
MS 422.6 (MH$^+$).

INTERMEDIATE 13

2-(4-Benzylpiperidine-1-sulfonyl)benzoic acid methyl ester

From 2-chlorosulfonylbenzoic acid methyl ester (587 mg) and 4-benzyl-piperidine (350 mg) as a brown oil (652 mg, 87%).

$R_f$ 0.35 (1:1 diethyl ether/hexane);
MS 373 (M$^+$).

INTERMEDIATE 14

2-[(4-Methoxyphenyl)methyl-sulfamoyl]benzoic acid methyl ester

From 2-chlorosulfonylbenzoic acid methyl ester (587 mg) and N-(4-methoxyphenyl)-methylamine (0.27 g) as a brown oil (0.53 g, 79%).

$R_f$ 0.3 (1:1 diethyl ether/hexane);
MS 335 (M$^+$).

INTERMEDIATE 15

2-[4-(Pyridin-2-yl)piperazine-1-sulfonyl]benzoic acid methyl ester

From 2-chlorosulfonylbenzoic acid methyl ester (469 mg) and 1-pyridin-2-yl-piperazine (408 mg) as a yellow oil (0.63 g, 87%).

$R_f$ 0.35 (1:1 diethyl ether/hexane);
MS 361 (M$^+$).

INTERMEDIATE 16

2-(3,4-Dihydro-1H-isoquinoline-2-sulfonyl)benzoic acid methyl ester

From 2-chlorosulfonylbenzoic acid methyl ester (469 mg) and 1,2,3,4-tetrahydro-isoquinoline (333 mg) as a yellow oil (475 mg, 71%).

$R_f$ 0.25 (1:1 diethyl ether/hexane);
MS 331 (M$^+$)

INTERMEDIATE 17

2-(Acetylsulfanylmethyl)benzoic acid methyl ester

To a stirred solution of Intermediate 4 (2.92 g) in DMF (5 ml) at 0° C. was added potassium thioacetate (1.60 g). Stirring was continued for 30 mins at this temperature and then stirred at RT for a further 1 h. The mixture was poured into ice/water (100 ml) and extracted with diethyl ether (3×50 ml). The resulting ethereal extracted was further washed with saturated aqueous sodium hydrogen carbonate solution (50 ml), water (50 ml) and brine (50 ml). The organic layer was then dried (Na$_2$SO$_4$), filtered and the solvent removed under reduced pressure to give a brown oil. Purification by silica gel column chromatography, eluting with 5:1 hexane/diethyl ether gave the title compound (2.05 g, 75%) as a colourless oil which subsequently solidified.

$R_f$ 0.25 (5:1 hexane/diethyl ether);
MS 247 ([M+Na]$^+$).

INTERMEDIATE 18

2-(Chlorosulfonylmethyl)benzoic acid methyl ester

To a stirred solution of Intermediate 17 (2 g) in glacial acetic acid (1 ml) at 5° C. was added water (100 ml). Through this suspension was bubbled chlorine gas for 20 minutes until a finely divided green suspension developed. Addition of gas was stopped and stirring continued for 30 mins before dichloromethane (150 ml) was added. The organic was then collected and washed with saturated aqueous sodium hydrogen carbonate solution (50 ml), water (50 ml) and brine (50 ml). The resulting extracts were dried (Na$_2$SO$_4$) and the solvent removed under reduced pressure to give the title compound (0.95 g, 85%) as a white solid.

$R_f$ 0.48 (5:1 hexane/diethyl ether).

INTERMEDIATE 19

2-[4-(4-Chlorophenyl)piperazine-1-sulfonylmethyl] benzoic acid methyl ester

To stirred suspension of 4-(4-chlorophenyl)piperazine dihydrochloride (1.1 g) in dichloromethane (10 ml) at 0° C.

was added triethylamine (2 ml). After 15 mins, a solution of Intermediate 18 (0.49 g) in dichloromethane (5 ml) was added. Stirring was continued at this temperature for 30 mins and then at RT for 1 hr. The reaction mixture was diluted with dichloromethane (100 ml) and then washed with aqueous 10% citric acid (3×50 ml), saturated aqueous sodium hydrogen carbonate solution (3×50 ml), water (3×50 ml) and brine (50 ml). The organic layer was then dried ($Na_2SO_4$), filtered and the solvent removed under reduced pressure to give the title compound (0.24 g, 48%) as a yellow oil.

$R_f$ 0.55 (1:1 hexane/diethyl ether);
MS 409.5 ($MH^+$).

Similarly prepared were:

INTERMEDIATE 20

2-[4-(4-Chlorophenoxy)piperidine-1-sulfonylmethyl]benzoic acid methyl ester

From Intermediate 18 (621 mg) and 4-(4-chlorophenoxy)piperidine (524 mg) as a yellow oil (0.16 g, 18%).

$R_f$ 0.36 (1:1 diethyl ether/hexane);
MS 423.5 ($MH^+$).

INTERMEDIATE 21

2-[4-(4-Chlorobenzoyl)piperidine-1-sulfonylmethyl]benzoic acid methyl ester

From Intermediate 18 (621 mg) and 4-(4-chlorobenzoyl)piperidine (520 mg) as a yellow oil (0.05 g, 6%).

$R_f$ 0.39 (1:1 diethyl ether/hexane).

INTERMEDIATE 22

2-(3,4-Dihydro-1-H-isoquinoline-2-sulfonylmethyl)benzoic acid methyl ester

From Intermediate 18 (621 mg) and 3,4-dihydro-1-H-isoquinoline (266 mg) as a colourless oil (0.05 g, 7%).

$R_f$ 0.38 (1:1 diethyl ether/hexane);
MS 346 ($MH^+$).

INTERMEDIATE 23

2[(Benzofuran-2-ylmethyl-methyl-sulfamoyl)methyl]benzoic acid methyl ester

From Intermediate 18 (0.45 g) and Intermediate 6 (0.30 g) as a yellow oil (0.23 g, 34%).

$R_f$ 0.16 (1:1 diethyl ether/hexane);
MS 373 ($M^+$).

INTERMEDIATE 24

2-[4-(Pyridin-2-yl)piperazine-1-sulfonylmethyl)benzoic acid methyl ester

From Intermediate 18 (0.50 g) and 1-(pyridin-2-yl)piperazine (408 mg) as a beige solid (628 mg, 66%).

$R_f$ 0.21 (1:1 diethyl ether/hexane);
MS 375 ($M^+$).

INTERMEDIATE 25

2-[4-[5-(Trifluoromethyl)pyridin-2-yl]piperazine-1-sulfonylmethyl]benzoic acid methyl ester From Intermediate 18 (0.50 g) and (5-trifluoromethylpyridin-2-yl)piperazine as a beige solid (712 mg, 65%).

$R_f$ 0.13 (1:1 diethyl ether/hexane);
MS 443 ($M^+$).

INTERMEDIATE 26

2-{4-[4-(1,1-Difluoromethoxy)phenyl]piperazine-1-sulfonylmethyl}benzoic acid methyl ester From Intermediate 18 (0.3 g) and Intermediate 3 (0.451 g) as a beige solid (369 mg, 79%).

$R_f$ 0.5 (diethyl ether);
MS 440 ($M^+$).

INTERMEDIATE 27

2-{[(4-Methoxyphenyl)methylsulfamoyl]methyl}benzoic acid methyl ester

From Intermediate 18 (0.5 g) and 4-methoxyphenyl-N-methylamine (278 mg) as a brown oil (479 mg, 62%).

$R_f$ 0.57 (1:1 diethyl ether/hexane);
MS 350 ($M^+$).

INTERMEDIATE 28

{2-[4-(4-Chlorophenyl)piperazine-1-sulfonyl]phenyl}acetonitrile

To stirred suspension of 4-(4-chlorophenyl)piperazine dihydrochloride (400 mg) in dichloromethane (25 ml) at RT was added triethylamine (0.78 ml). After 15 mins, a solution of Intermediate 5 (500 mg) in dichloromethane (5 ml) was added. Stirring was continued for 2 h. The reaction mixture was diluted with dichloromethane (50 ml) and then washed with aqueous citric acid (10%, 2×20 ml), saturated aqueous sodium hydrogen carbonate solution (2×20 ml), water (2×20 ml) and brine (20 ml). The organic layer was then dried ($MgSO_4$), filtered and the solvent removed under reduced pressure. The residue was chromatographed (2:1 hexane/ethyl acetate) to give the title compound (0.43 g, 61%) as an off-white solid.

$R_f$ 0.37 (2:1 hexane/ethyl acetate).

Similarly prepared were:

INTERMEDIATE 29

2-Cyanomethyl-N-(4-methoxyphenyl)-N-methyl-benzenesulfonamide

From Intermediate 5 (431 mg) and N-(4-methoxyphenyl)methylamine (274 mg) as an off-white solid (235 mg, 37%).

$R_f$ 0.23 (2:1 hexane/ethyl acetate);
MS 317 ($MH^+$).

INTERMEDIATE 30

{2-[4-(4-Difluoromethoxyphenyl)piperazine-1-sulfonyl]phenyl}-acetonitrile

From Intermediate 3 (431 mg) and 1-(4-difluoromethoxyphenyl)piperazine (456 mg) as a white solid (540 mg, 66%).

$R_f$ 0.24 (2:1 hexane/ethyl acetate);
MS 407 ($MH^+$).

INTERMEDIATE 31

{2-[4-(5-Trifluoromethylpyridin-2-yl)piperazine-1-sulfonyl]phenyl}acetonitrile

From Intermediate 11 (433 mg) and 1-[5-(trifluoromethyl)pyrid-2-yl]piperazine (462 mg) as a white solid (683 mg, 83%).

$R_f$ 0.37 (2:1 hexane/ethyl acetate);
MS 410 (MH$^+$).

INTERMEDIATE 32

2-{2-[4-(4-Chlorophenyl)piperazine-1-sulfonyl]phenyl}-3-methyl-butyronitrile

Sodium hydride (43 mg of a 60% dispersion in oil) was added to a solution of Intermediate 28 (400 mg) in THF (20 ml). After stirring for 5 min, isopropyl iodide (271 mg) was added. The mixture was stirred at room temperature for 5 min and then at reflux for 30 min. It was cooled to room temperature and diluted with water (30 ml) before being extracted with ethyl acetate (3×30 ml). The combined extracts were washed with water (2×20 ml) and brine (20 ml), then dried (MgSO$_4$), evaporated and chromatographed (4:1 hexane/ethyl acetate) to give the title compound (235 mg, 53%) as a white foam.

$R_f$ 0.42 (3:1 hexane:diethyl ether);
MS 417 (MH$^+$).

EXAMPLE 1

2-[4-(4-Chlorophenyl)piperazine-1-sulfonyl]benzoic acid

To a stirred solution of Intermediate 7 (2.00 g) in a mixture of methanol (50 ml) and THF (30 ml) was added a solution of lithium hydroxide monohydrate (1.06 g) in water (20 ml). The resulting suspension was heated to reflux for 2 h. On cooling the solvent was removed under reduced pressure and the resulting residue partitioned between diethyl ether (50 ml) and water (100 ml). The aqueous layer was collected and acidified to pH 5 with citric acid. The aqueous mixture was then extracted with ethyl acetate (4×50 ml) and the combined organic layers washed with water (40 ml) and brine (40 ml). Following drying (Na$_2$SO$_4$), the solvent was removed under reduced pressure to give the title compound (1.48 mg, 77%) as an off-white solid.

$R_f$ 0.12 (1:1 hexane:diethyl ether);
MS 381 (MH$^+$).

Similarly prepared were:

EXAMPLE 2

2-[4-(4-Chlorophenoxy)piperidine-1-sulfonyl]benzoic acid

From Intermediate 8 (830 mg) as a white foam (0.53 g, 66%).

$R_f$ 0.58 (10% methanol/dichloromethane);
MS 396.5 (MH$^+$).

EXAMPLE 3

2-[4-(4-Difluoromethoxyphenyl)piperazine-1-sulfonyl]benzonic acid

From Intermediate 9 (850 mg) as a beige solid (0.53 g, 80%).

$R_f$ 0.35 (10% methanol/dichloromethane);
MS 412 (M$^+$).

EXAMPLE 4

2-[4-(3,5-Dichlorophenyl)piperazine-1-sulfonyl]benzoic acid

From Intermediate 10 (760 mg) as a yellow solid (0.55 g, 75%).

$R_f$ 0.52 (10% methanol/dichloromethane);
MS 415 (M$^+$).

EXAMPLE 5

2-[4-(4-Trifluoromethylpyridin-2-yl)piperazine-1-sulfonyl]benzoic acid

From Intermediate 11 (830 mg) as a white foam (0.58 g, 93%).

$R_f$ 0.58 (10% methanol/dichloromethane);
MS 416 (MH$^+$).

EXAMPLE 6

2-[4-(4-Chlorobenzoyl)piperidine-1-sulfonyl]benzoic acid

From Intermediate 12 (266 mg) as a white foam (0.18 g, 70%).

$R_f$ 0.46 (10% methanol/dichloromethane);
MS 408.5 (MH$^+$).

EXAMPLE 7

2-(4-Benzylpiperidine-1-sulfonyl)benzoic acid

From Intermediate 13 (652 mg) as a cream solid (430 mg, 68%).

$R_f$ 0.35 (10% methanol/dichloromethane);
MS 359 (M$^+$).

EXAMPLE 8

2[(4-Methoxyphenyl)methylsulfamoyl]benzoic acid

From Intermediate 14 (242 mg) as a beige solid (148 mg, 64%).

$R_f$ 0.1 (5% methanol/dichloromethane);
MS 321 (M$^+$).

EXAMPLE 9

2-[(4-(Pyridin-2-yl)piperazine-1-sulfonyl]benzoic acid

From Intermediate 15 (630 mg) as a white solid (200 mg, 35%).

$R_f$ 0.20 (10% methanol/dichloromethane);
MS 347 (M$^+$).

EXAMPLE 10

2-(3,4-Dihydro-1H-isoquinoline-2-sulfonyl)benzoic acid

From Intermediate 16 (475 mg) as a white solid (368 mg, 81%).

$R_f$ 0.3 (5% methanol/dichloromethane);
MS 317 (M$^+$).

EXAMPLE 11

N-Hydroxy-2-[4-(4-Chlorophenyl)piperazine-1-sulfonyl]benzamide

To a stirred solution of Example 1 (1.00 g) and oxalyl chloride (1.15 ml) in dichloromethane (30 ml) at RT was added DMF (1 drop). Stirring was continued at this temperature for 1 h before the solvent was removed under reduced pressure. The residue was azeotroped with 1:1 hexane/dichloromethane (3×60 ml) and then dispersed in THF. The suspension was cooled to 0° C. and treated with a solution of hydroxylamine (0.8 ml, 50% w/w). The reaction was stirred for 1 h at RT and then the solvent was removed under reduced pressure. The residue was treated with water (30 ml) and stirred for 1.5 h. The solid was collected and dried to give the title compound (1.00 g, 96%) as a white solid.

$R_f$ 0.56 (ethyl acetate);
MS 410.7 (MH$^+$).
Similarly prepared were:

EXAMPLE 12

N-Hydroxy-2-[4-(4-Chlorophenoxy)piperidine-1-sulfonyl]benzamide

From Example 2 (0.54 g) as a beige foam (0.3 g, 54%).
$R_f$ 0.48 (10% methanol/dichloromethane);
MS 411 (MH$^+$).

EXAMPLE 13

N-Hydroxy-2-[4-(4-Difluoromethoxyphenyl)piperazine-1-sulfonyl]benzamide

From Example 3 (0.65 g) as a beige foam (0.28 g, 41%).
$R_f$ 0.42 (10% methanol/dichloromethane);
MS 427 (M$^+$).

EXAMPLE 14

N-Hydroxy-2-[4-(3,5-Dichlorophenyl)piperazine-1-sulfonyl]benzamide

From Example 4 (0.55 g) as a beige solid (0.29 g, 52%).
$R_f$ 0.51 (10% methanol/dichloromethane);
MS 430 (M$^+$).

EXAMPLE 15

N-Hydroxy-2-[4-(4-Trifluoromethylpyridin-2-yl)piperazine-1-sulfonyl]benzamide

From Example 5 (0.75 g) as a pale yellow solid (0.29 g, 37%).
$R_f$ 0.6 (10% methanol/dichloromethane);
MS 430 (M$^+$).

EXAMPLE 16

N-Hydroxy-2-[4-(4-Chlorobenzoyl)piperidine-1-sulfonyl]benzamide

From Example 6 (460 mg) as a white foam (0.12 g, 25%).
$R_f$ 0.25 (5% methanol/dichloromethane);
MS 423.5 (MH$^+$).

EXAMPLE 17

N-Hydroxy-2-(4-Benzylpiperidine-1-sulfonyl)benzamide

From Example 7 (400 mg) as a beige solid (56 mg, 13%).
$R_f$ 0.45 (10% methanol/dichloromethane);
MS 375.5 (MH$^+$).

EXAMPLE 18

N-Hydroxy-2-[(4-methoxyphenyl)methylsulfamoyl]benzamide

From Example 8 (145 mg) as a beige solid (33 mg, 20%).
$R_f$ 0.25 (5% methanol/dichloromethane);
MS 337 (MH$^+$).

EXAMPLE 19

N-Hydroxy-2-[4-(pyridin-2-yl)piperazine-1-sulfonyl]benzamide

From Example 9 (200 mg) as a white solid (43 mg, 21%).
$R_f$ 0.42 (10% methanol/dichloromethane).

EXAMPLE 20

2-(3,4-Dihydro-1H-isoquinoline-2-sulfonyl)-N-hydroxybenzamide

From Example 10 (365 mg) as a white solid (59 mg, 15%).
$R_f$ 0.44 (10% methanol/dichloromethane);
MS 332 (M$^+$).

EXAMPLE 21

2-[4-(4-Chlorophenyl)piperazine-1-sulfonylmethyl]benzoic acid

To a stirred solution of Intermediate 19 (0.25 g) in 1:1:1 methanol/THF/water (30 ml) was added lithium hydroxide monohydrate (0.5 g). The resulting suspension was heated to reflux for 2.5 h. On cooling the solvent was removed under reduced pressure and the resulting residue partitioned between diethyl ether (50 ml) and water (20 ml). The aqueous layer was collected and acidified to pH 5 with citric acid. The aqueous mixture was then extracted with ethyl acetate (3×50 ml) and the combined organic layers washed with water (10 ml) and brine (10 ml). Following drying (Na$_2$SO$_4$), the solvent was removed under reduced pressure to give a pale brown oil. The material was dissolved in a minimum volume of ethyl acetate and treated with excess hexane to give a precipitate. Filtration and washing with diethyl ether (3×5 ml) gave the title compound (113 mg, 46%) as a white solid.

$R_f$ 0.62 (10% methanol/dichloromethane);
MS 395.5 (MH$^+$).
Similarly prepared were:

EXAMPLE 22

2-[4-(4-Chlorophenoxy)piperidine-1-sulfonylmethyl]benzoic acid

From Intermediate 20 (300 mg) as a white solid (240 mg, 44%).
$R_f$ 0.35 (10% methanol/dichloromethane).

EXAMPLE 23

2-[4-(4-Chlorobenzoyl)piperidine-1-sulfonylmethyl]benzoic acid

From Intermediate 21 (400 mg) as a white solid (350 mg, 90%).
$R_f$ 0.30 (10% methanol/dichloromethane);
MS 422 (MH$^+$).

EXAMPLE 24

2-(3,4-Dihydro-1H-isoquinoline-2-sulfonylmethyl) benzoic acid

From Intermediate 22 (400 mg) as a white solid (261 mg, 68%).

$R_f$ 0.10 (5% methanol/dichloromethane);
MS 332 (MH$^+$).

EXAMPLE 25

2-[(Benzofuran-2-ylmethyl-methyl-sulfamoyl) methyl]benzoic acid

From Intermediate 23 (232 mg) as a white solid (57 mg, 25%).

$R_f$ 0.15 (5% methanol/dichloromethane);
MS 358 (MH$^-$).

EXAMPLE 26

2-[4-(Pyridin-2-yl)piperazine-1-sulfonylmethyl] benzoic acid

From Intermediate 24 (686 mg) as a white solid (104 mg, 15%).

$R_f$ 0.21 (5% methanol/dichloromethane);
MS 362 (MH$^+$).

EXAMPLE 27

2-[4-(5-Trifluoromethylpyridin-2-yl)piperazine-1-sulfonylmethyl]benzoic acid

From Intermediate 25 (712 mg) as a white solid (110 mg, 16%).

$R_f$ 0.26 (10% methanol/dichloromethane);
MS 430 (MH$^+$).

EXAMPLE 28

2-[4-[4-(1,1-Difluoromethoxy)phenyl]piperazine-1-sulfonylmethyl]benzoic acid

From Intermediate 26 (367 mg) as a pink solid (176 mg, 49%).

$R_f$ 0.30 (10% methanol/dichloromethane);
MS 427 (MH$^+$).

EXAMPLE 29

2-([(4-Methoxyphenyl)methyl-sulfamoyl]methyl) benzoic acid

From Intermediate 27 (429 mg) as a white solid (309 mg, 75%).

$R_f$ 0.30 (10% methanol/dichloromethane);
MS 334 (MH$^-$).

EXAMPLE 30

2-[4-(4-Chlorophenyl)piperazine-1-sulfonylmethyl]-N-hydroxybenzamide

To a stirred solution of Example 21 (0.16 g) and oxalyl chloride (1 ml) in dichloromethane (10 ml) at RT was added DMF, with evolution of gas. Stirring was continued at this temperature for 2 h before the solvent was removed under reduced pressure. The residue was azeotroped with 1:1 hexane/dichloromethane (3×20 ml) and then dispersed in THF. The suspension was cooled to 0° C. and treated with a 50% by weight solution of hydroxylamine in water (1 ml). The reaction was stirred for 1 h at RT and then the solvent was removed under reduced pressure. The residue was partitioned between ethyl acetate (50 ml) and water (20 ml). Collection of the organic layer was followed by washing of this layer with saturated aqueous sodium hydrogen carbonate solution (10 ml), water (5 ml) and brine (10 ml). The resulting extracts were dried (Na$_2$SO$_4$) and the solvent removed under reduced pressure to give a pale brown oil. This material was dissolved in a minimum volume of ethyl acetate and then treated with excess hexane to give a precipitate. The solid was collected by filtration, washing with diethyl ether (3×10 ml) to give the title compound (0.02 g, 14%) as a beige solid.

$R_f$ 0.62 (10% methanol/dichloromethane);
MS 410.7 (MH$^+$).

Similarly prepared were:

EXAMPLE 31

2-[4-(4-Chlorophenoxy)piperidine-1-sulphonylmethyl]-N-hydroxybenzamide

From Example 22 (240 mg) as a white solid (25 mg, 10%).

$R_f$ 0.25 (5% methanol/dichloromethane);
MS 425.6 (MH$^+$).

EXAMPLE 32

2-[4-(4-Chlorobenzoyl)piperidine-1-sulfonylmethyl]-N-hydroxybenzamide

From Example 23 (370 mg) as a beige solid (15 mg, 4%).

$R_f$ 0.3 (5% methanol/dichloromethane);
MS 437.5 (MH$^+$).

EXAMPLE 33

2-(3,4-Dihydro-1H-isoquinoline-2-sulfonylmethyl)-N-hydroxybenzamide

From Example 24 (261 mg) as a white solid (75 mg, 30%).

$R_f$ 0.21 (5% methanol/dichloromethane);
MS 347 (MH$^+$).

EXAMPLE 34

2-[(Benzofuran-2-ylmethyl-methyl-sulfamoyl) methyl]-N-hydroxybenzamide

From Example 25 (50 mg) as a white solid (22 mg, 44%).

$R_f$ 0.21 (5% methanol/dichloromethane);
MS 375 (MH$^+$).

EXAMPLE 35

N-Hydroxy-2-[4-(5-trifluromethylpyridin-2-yl) piperazine-1-sulfonylmethyl]benzamide From Example 27 (100 mg) as a white solid (42 mg, 40%).

$R_f$ 0.16 (5% methanol/dichloromethane);
MS 443 (MH$^-$).

EXAMPLE 36

2-{4-[4-(1,1-Difluoromethoxy)phenyl]piperazine-1-sulphonylmethyl}-N-hydroxybenzamide From Example 28 (166 mg) as a white solid (93 mg, 54%).

$R_f$ 0.23 (5% methanol/dichloromethane);
MS 440 (MH$^-$).

EXAMPLE 37

N-Hydroxy-2-2-{[(4-methoxyphenyl)methyl-sulfamoyl]methyl}benzamide

From Example 29 (289 mg) as a white solid (138 mg, 45%).

$R_f$ 0.28 (10% methanol/dichloromethane);
MS 349 (MH$^+$).

EXAMPLE 38

{2-[4-(4-Chlorophenyl)piperazine-1-sulfonyl]phenyl}acetic acid

A mixture of Intermediate 22 (417 mg) and 1M sodium hydroxide solution (30 ml) was refluxed for 72 hours. The mixture was cooled and acidified to pH1 with 6M hydrochloric acid. The mixture was extracted with ethyl acetate (4×20 ml) and the combined extracts were washed with water (2×20 ml), brine (20 ml) and dried (MgSO$_4$). The mixture was filtered and evaporated to dryness to give the title compound as a pale yellow solid (360 mg, 82%).

$R_f$ 0.23 (1:1 ethyl acetate/hexane);
MS 395 (MH$^+$).
Similarly prepared were:

EXAMPLE 39

{2-[(4-Methoxyphenyl)methyl-sulfamoyl]phenyl}acetic acid

From Intermediate 23 (230 mg) as a white solid (242 mg, 99%).

$R_f$ 0.35 (2:1 ethyl acetate/hexane);
MS 336 (MH$^+$).

EXAMPLE 40

{2-[4-(4-Difluoromethoxyphenyl)piperazine-1-sulfonyl]phenyl}acetic acid

From Intermediate 30 (530 mg) as a brown oil (145 mg, 26%).

$R_f$ 0.10 (2:1 ethyl acetate/hexane);
MS 426 (MH$^+$).

EXAMPLE 41

{2-[4-(5-Trifluoromethylpyridin-2-yl)piperazine-1-sulfonyl]phenyl}acetic acid

From Intermediate 31 (660 mg) as an off white solid (609 mg, 85%).

$R_f$ 0.25 (10:1 dichloromethane/methanol);
MS 430 (MH$^+$).

EXAMPLE 42

{4,5-Dimethoxy-2-[4-(5-trifluoromethylpyridin-2-yl)piperazine-1-sulfonyl]phenyl}acetic acid {4,5-Dimethoxy-2-[4-(5-trifluoromethylpyridin-2-yl)piperazine-1-sulfonyl]phenyl}acetic acid methyl ester (0.3 g) was taken up in methanol (10 ml), tetrahydrofuran (10 ml) and water (10 ml). Lithium hydroxide (125 mg) was added and the reaction stirred at RT for 16 hrs. The reaction was diluted with water (10 ml), its volume reduced to one third in vacuo, and the reaction extracted with diethyl ether (3×15 ml). The aqueous layer was acidified to pH 4 with 2M hydrochloric acid and extracted with ethyl acetate (4×25 ml). The combined ethyl acetate extracts were washed with water (25 ml) and brine (25 ml) and dried over sodium sulphate. The solvent was removed in vacuo to yield the title compound as a white solid (291 mg, 100%).

$R_f$ 0.19 (2:1 ethyl acetate/hexane);
MS 490 (MH$^+$).

EXAMPLE 43

2-{2-[4-(4-Chlorophenyl)piperazine-1-sulfonyl]phenyl}-3-methylbutyric acid

Intermediate 32 (0.23 g) was taken up in ethylene glycol (25 ml) with potassium hydroxide (155 mg) and heated at 150° C. for 72 hrs. After cooling the reaction was diluted with water (50 ml), and extracted with diethyl ether (3×15 ml). The aqueous layer was acidified to pH 1 with 2M hydrochloric acid, and extracted with ethyl acetate (4×25 ml). The combined ethyl acetate extracts were washed with water (2×25 ml), brine (25 ml) and dried over magnesium sulphate. The solvent was removed in vacuo to yield a brown oil which was purified by flash chromatography (eluent 2:1 hexane/ethyl acetate) to yield the title compound as a white solid (152 mg, 63%).

$R_f$ 0.18 (1:2 ethyl acetate/hexane);
MS 437 (MH$^+$).

EXAMPLE 44

[2-(Benzofuran-2-ylmethyl-methyl-sulfamoyl)phenyl]acetic acid

To stirred suspension of Intermediate 6 (322 mg) in dichloromethane (20 ml) at RT was added triethylamine (0.84 ml). After 15 min, a solution of Intermediate 5 (431 mg) in dichloromethane (5 ml) was added. Stirring was continued for 1 h before the solvent was removed in vacuo. The residue was treated with sodium hydroxide solution (3M, 20 ml) and refluxed for 24 h. The mixture was cooled, washed with diethyl ether (20 ml) and acidified to pH3 with 2M hydrochloric acid and extracted with ethyl acetate (4×20 ml). The combined ethyl acetate layers were washed with water (20 ml), brine (20 ml) and dried over magnesium sulphate. Filtration and evaporation of the solvent yielded the title compound as an off-white solid (159 mg, 22%).

$R_f$ 0.30 (2:1 ethyl acetate/hexane);
MS 360 (MH$^+$).
Similarly prepared were:

EXAMPLE 45

[2-[4-(Pyridin-2-yl)piperazine-1-sulfonyl]phenyl]acetic acid

From Intermediate 5 (431 mg) and 4-(2-pyridinyl)piperazine (326 mg) as an off-white solid (335 mg, 46%).

$R_f$ 0.05 (2:1 ethyl acetate/hexane);
MS 362 (MH$^+$).

EXAMPLE 46

{2-[4-(3,5-Dichlorophenyl)piperazine-1-sulfonyl]phenyl}acetic acid

From Intermediate 5 (431 mg) and 4-(3,5-dichlorophenyl)piperazine (462 mg) as an off-white solid (265 mg, 31%).

$R_f$ 0.43 (2:1 ethyl acetate/hexane);
MS 430 (MH$^+$).

EXAMPLE 47

{2-[4-(4-Chlorophenoxy)piperidine-1-sulfonyl]phenyl}acetic acid

From Intermediate 5 (431 mg) and 4-(4-chlorophenoxy)piperidine (496 mg) as an off-white solid (206 mg, 25%).
$R_f$ 0.33 (2:1 ethyl acetate/hexane);
MS 410 (MH$^+$).

EXAMPLE 48

[2-(4-Chlorobenzoylpiperidine-1-sulfonyl)phenyl]acetic acid

From Intermediate 5 (431 mg) and 4-(4-chlorobenzoyl)piperidine (520 mg) as an off-white solid (377 mg, 45%).
$R_f$ 0.26 (2:1 ethyl acetate/hexane);
MS 422 (MH$^+$).

EXAMPLE 49

[2-(3,4-Dihydro-1H-isoquinoline-2-sulfonyl)phenyl]acetic acid

From Intermediate 5 (431 mg) and 3,4-dihydro-1H-isoquinoline (266 mg) as an off-white solid (416 mg, 63%).
$R_f$ 0.38 (2:1 ethyl acetate/hexane);
MS 332 (MH$^+$).

EXAMPLE 50

{2-[4-(4-Chlorophenyl)piperazine-1-sulfonyl]phenyl}-N-hydroxyacetamide

To a stirred solution of Example 38 (0.35 g) and oxalyl chloride (2 ml) in dichloromethane (20 ml) at RT was added DMF, with evolution of gas. Stirring was continued at this temperature for 2 h before the solvent was removed under reduced pressure. The residue was azeotroped with 1:1 hexane/dichloromethane (3×20 ml) and then dispersed in THF. The suspension was cooled to 0° C. and treated with a 50% by weight solution of hydroxylamine in water (1 ml). The reaction was stirred for 1 hour at RT and then the solvent was removed under reduced pressure. The residue partitioned between ethyl acetate (50 ml) and water (20 ml). Collection of the organic layer was followed by washing of this layer with saturated aqueous sodium hydrogen carbonate solution (10 ml), water (5 ml) and brine (10 ml). The resulting extracts were dried over sodium sulphate and the solvent removed under reduced pressure to give a pale brown oil. This material was dissolved in a minimum volume of ethyl acetate and then treated with excess hexane to give a precipitate. The solid was collected by filtration, washing with diethyl ether (3×10 ml) to give the title compound (238 mg, 66%) as an off-white solid.
$R_f$ 0.42 (5:1 ethyl acetate/hexane);
MS 410 (MH$^+$).
Similarly prepared were:

EXAMPLE 51

{2-[(4-Methoxyphenyl)methyl-sulfamoyl]phenyl}-N-hydroxyacetamide

From Example 39 (229 mg) as an off-white solid (218 mg, 91%).
$R_f$ 0.36 (10:1 dichloromethane/methanol);
MS 351 (MH$^+$).

EXAMPLE 52

2-{2-[4-(4-Difluoromethoxyphenyl)piperazine-1-sulfonyl]phenyl}-N-hydroxyacetamide From Example 40 (135 mg) as a brown solid (86 mg, 61%).
$R_f$ 0.38 (10:1 dichloromethane/methanol);
MS 441 (MH$^+$).

EXAMPLE 53

N-Hydroxy-2-{2-[4-(5-trifluoromethylpyridin-2-yl)piperazine-1-sulfonyl]phenyl}acetamide From Example 41 (135 mg) as an off-white solid (503 mg, 82%).
$R_f$ 0.42 (10:1 dichloromethane/methanol);
MS 444 (MH$^+$).

EXAMPLE 54

2-{4,5-Dimethoxy-2-[4-(5-trifluoromethylpyridin-2-yl)-piperazine-1-sulfonyl]phenyl}-N-hydroxyacetamide From Example 42 (260 mg) as a white solid (237 mg, 88%).
$R_f$ 0.29 (10:1 dichloromethane/methanol);
MS 504 (MH$^+$).

EXAMPLE 55

2-{2-[4-(4-Chlorophenyl)piperazine-1-sulfonyl]phenyl}-N-hydroxy-3-methylbutyramide From Example 43 (115 mg) as a white solid (113 mg, 95%).
$R_f$ 0.37 (10:1 dichloromethane/methanol);
MS 451 (MH$^+$).

EXAMPLE 56

[2-(Benzofuran-2-ylmethyl-methyl-sulfamoyl)phenyl]-N-hydroxyacetamide

From Example 44 (155 mg) as an off-white solid (106 mg, 66%).
$R_f$ 0.37 (10:1 dichloromethane/methanol);
MS 375 (MH$^+$).

EXAMPLE 57

[2-[-(4-Pyridin-2-yl)piperazine-1-sulfonyl]phenyl]-N-hydroxyacetamide

From Example 45 (330 mg) as an off-white solid (306 mg, 86%).
$R_f$ 0.27 (10:1 dichloromethane/methanol);
MS 389 (MH$^+$).

EXAMPLE 58

2-{2-[4-(3,5-Dichlorophenyl)piperazine-1-sulfonyl]phenyl}-N-hydroxyacetamide

From Example 46 (260 mg) as an off-white solid (230 mg, 86%).

$R_f$ 0.36 (10:1 dichloromethane/methanol);
MS 445 (MH$^+$).

EXAMPLE 59

{2-[4-(4-Chlorophenoxy)piperidine-1-sulfonyl]
phenyl}-N-hydroxyacetamide

From Example 47 (201 mg) as an off-white solid (94 mg, 45%).

$R_f$ 0.37 (10:1 dichloromethane/methanol);
MS 424 (MH$^+$).

EXAMPLE 60

[2-(4-Chlorobenzoylpiperidine-1-sulfonyl)phenyl]-
N-hydroxyacetamide

From Example 48 (372 mg) as an off-white solid (290 mg, 75%).

$R_f$ 0.36 (10:1 dichloromethane/methanol);
MS 437 (MH$^+$).

EXAMPLE 61

2-(2-{4-[(4-Chlorophenyl)hydroxyiminomethyl]
piperidine-1-sulfonyl}phenyl)-N-hydroxyacetamide From Example 48 (372 mg) as an off-white solid (32 mg, 8%).

$R_f$ 0.40 (10:1 dichloromethane/methanol);
MS 451 (MH$^+$).

EXAMPLE 62

[2-(3,4-Dihydro-1H-isoquinoline-2-sulfonyl)
phenyl]-N-hydroxyacetamide

From Example 49 (300 mg) as an off-white solid (212 mg, 74%).

$R_f$ 0.37 (10:1 dichloromethane/methanol);
MS 346 (MH$^+$).

EXAMPLE 63

3-[4-(4-Chlorophenyl)piperazine-1-sulfonyl]benzoic acid

To a suspension of 1-(4-chlorophenyl)piperazine dihydrochloride (539 mg) and 3-(chlorosulfonyl)benzoic acid (441 mg) in dichloromethane (50 ml) was added diisopropylethylamine (0.8 ml). After stirring overnight at room temperature the reaction mixture was washed with 2N HCl (3×25 ml) and brine (25 ml), dried over MgSO$_4$, filtered and evaporated to give the title compound as white solid (290 mg, 38%).

MS 381 (M$^+$).

EXAMPLE 64

3-[4-(4-Chlorophenyl)piperazine-1-sulfonyl]-N-
hydroxybenzamide

To a suspension of Example 63 (190 mg) was added O-(tert-butyldimethylsilyl)-hydroxylamine (81 mg) and 1-(3-dimethylaminopropyl)-3-ethylcarbodiimide hydrochloride (96 mg). After stirring overnight at room temperature ethyl acetate (100 mL) was added and the organic layer was washed with water (2×25 ml), saturated NaHCO$_3$ (2×25 ml) and water (25 ml), dried over MgSO$_4$, filtered and evaporated. The colourless oil was dissolved in dichloromethane (20 ml) and treated with 1.0 M HCl solution in ether (1.5 ml). Filtration afforded the title compound as a white solid (100 mg, 50%).

$R_f$ 0.6 (10% methanol in dichloromethane);
MS 396 (M$^+$).

What is claimed is:

1. A compound of formula (I)

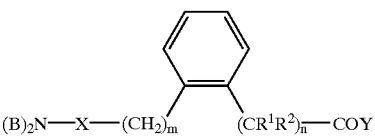

(I)

wherein
n=1;
m=1;
X is S(O)$_{1-2}$;
Y is NHOH;
R$^1$ is H, OR$^7$ or a group (optionally substituted with R$^3$) selected from C$_{1-6}$ alkyl, C$_{2-6}$ alkenyl, C$_{2-6}$ alkynyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl or C$_{1-6}$ alkyl-heterocycloalkyl; and
R$^2$ is H or C$_{1-6}$ alkyl;
or CR$^1$R$^2$ is cycloalkyl or heterocycloalkyl optionally substituted with R$^3$ or a group (optionally substituted with R$^3$) selected from C$_{1-6}$ alkyl, aryl, C$_{1-6}$ alkyl-aryl, heteroaryl or C$_{1-6}$ alkyl-heteroaryl;
R$^3$ is OR$^7$, COR$^7$, CO$_2$R$^8$, CON(R$^7$)$_2$, N(R$^7$)$_2$, NR$^7$COR$^7$, NR$^7$CON(R$^7$)$_2$, NR$^7$CO$_2$R$^8$, NR$^7$SO$_2$R$^8$, S(O)$_{0-2}$R$^8$, SO$_2$N(R$^7$)$_2$ or cycloimidyl (optionally substituted with R$^4$);
R$^4$ is C$_{1-6}$ alkyl;
B is H or a group (optionally substituted with R$^5$ or R$^6$) selected from C$_{1-6}$ alkyl, C$_{2-6}$ alkenyl, C$_{2-6}$ alkynyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl, C$_{1-6}$ alkyl-heterocycloalkyl, cycloalkenyl, or heterocycloalkenyl; and each instance of B may be the same or different;
or B—N—B is heterocycloalkyl optionally substituted with R$^5$, R$^6$, =O or =NOR$^5$;
R$^5$ is a group (optionally substituted with R$^6$) selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl or C$_{1-6}$ alkyl-heterocycloalkyl;
R$^6$ is a group selected from N(R$^7$)$_2$, NR$^7$COR$^7$, NR$^7$CON(R$^7$)$_2$, NR$^7$CO$_2$R$^8$, NR$^7$SO$_2$R$^8$, OR$^7$, COR$^7$, CO$_2$R$^4$, CON(R$^7$)$_2$, S(O)$_{0-2}$R$^8$ or SO$_2$N(R$^7$)$_2$;
R$^7$ is H or a group selected from C$_{1-6}$ alkyl, aryl, C$_{1-6}$ alkyl-aryl, heteroaryl, C$_{1-6}$ alkyl-heteroaryl, cycloalkyl, C$_{1-6}$ alkyl-cycloalkyl, heterocycloalkyl or C$_{1-6}$ alkyl-heterocycloalkyl, wherein said group is optionally substituted with R$^8$, COR$^8$, SO$_{0-2}$R$^8$, CO$_2$R$^8$, OR$^8$, CONR$^4$R$^8$, NR$^4$R$^8$ or SO$_2$NR$^4$R$^8$ and for each case of N(R$^7$)$_2$ the R$^7$ groups are the same or different or N($^7$)$_2$ is heterocycloalkyl optionally substituted with R$^8$, COR$^8$, S(O)$_{0-2}$R$^8$, CO$_2$R$^8$, OR$^8$, CONR$^4$R$^8$, NR$^4$R$^8$ or SO$_2$NR$^4$R$^8$; and
R$^8$ is C$_{1-6}$ alkyl, aryl, C$_{1-6}$ alkyl-aryl, heteroaryl or C$_{1-6}$ alkyl-heteroaryl;

or a salt, solvate, hydrate, N-oxide, protected amino, protected carboxy or protected hydroxamic acid derivative thereof.

2. The compound according to claim 1, wherein X is $SO_2$.

3. The compound according to claim 1, wherein B—N—B is optionally substituted heterocycloalkyl.

4. The compound according to claim 2, wherein B—N—B is optionally substituted heterocycloalkyl.

5. The compound according to claim 1, wherein B is H or a group (optionally substituted with $R^5$ or $R^6$) selected from $C_{1-6}$ alkyl, $C_{2-6}$ alkenyl, $C_{2-6}$ alkynyl, heteroaryl, $C_{1-6}$ alkyl-heteroaryl, cycloalkyl, $C_{1-6}$ alkyl-cycloalkyl, heterocycloalkyl, $C_{1-6}$ alkyl-heterocycloalkyl, cycloalkenyl or heterocycloalkenyl; and each instance of B may be the same or different.

6. The compound of claim 5, wherein B is H or a group (optionally substituted with $R^5$ or $R^6$) selected from $C_{1-6}$ alkyl, $C_{2-6}$ alkenyl, $C_{2-6}$ alkynyl, heterocycloalkyl, $C_{1-6}$ alkylcycloalkyl, heterocycloalkyl, $C_{1-6}$ alkyl-heterocycloalkyl, cycloalkenyl or heterocycloalkenyl; and each instance of B may be the same or different.

7. The compound according to claim 1, wherein neither B is H.

8. The compound of claim 7, wherein B—N—B is heterocycloalkyl substituted with a substituted $C_{1-6}$ alkyl-aryl group.

9. The compound according to claim 7, wherein B—N—B is heterocycloalkyl substituted with $NOR^5$, $R^6$ or a group (optionally substituted with $R^6$) selected from $C_{1-6}$ alkyl, aryl, heteroaryl, $C_{1-6}$ alkyl-heteroaryl, cycloalkyl, $C_{1-6}$ alkyl-cycloalkyl, heterocycloalkyl or $C_{1-6}$ alkyl-heterocycloalkyl.

10. The compound according to claim 7, wherein B—N—B is heterocycloalkyl substituted with $NOR^5$, $R^6$ or a group (optionally substituted with $R^6$) selected from $C_{1-6}$ alkyl, aryl, heteroaryl, cycloalkyl, $C_{1-6}$ alkyl-cycloalkyl, heterocycloalkyl or $C_{1-6}$ alkyl-heterocycloalkyl.

11. The compound according to claim 7, wherein B—N—B is heterocycloalkyl substituted with $NOR^5$, $R^6$ or a group (optionally substituted with $R^6$) selected from $C_{1-6}$ alkyl, cycloalkyl, $C_{1-6}$ alkyl-cycloalkyl, heterocycloalkyl or $C_{1-6}$ alkyl-heterocycloalkyl.

12. A compound selected from the group consisting of

N-hydroxy-2-[4-(4-chlorophenyl)piperazine-1-sulfonyl]benzamide,
N-hydroxy-2-[4-(4-chlorophenoxy)piperidine-1-sulfonyl]benzamide,
N-hydroxy-2-[4-(4-difluoromethoxyphenyl)piperazine-1-sulfonyl]benzamide,
N-hydroxy-2-[4-(3,5-dichlorophenyl)piperazine-1-sulfonyl]benzamide,
N-hydroxy-2-[4-(4-trifluoromethylpyridin-2-yl)piperazine-1-sulfonyl]benzamide,
N-hydroxy-2-[4-(4-chlorobenzoyl)piperidine-1-sulfonyl]benzamide,
N-hydroxy-2-(4-benzylpiperidine-1-sulfonyl)benzamide,
2-[4-(4-chlorophenyl)piperazine-1-sulfonylmethyl]-N-hydroxybenzamide,
{2-[4-(4-chlorophenyl)piperazine-1-sulfonyl]phenyl}-N-hydroxyacetamide,
[2-(benzofuran-2-yl-methyl-methyl-sulfamoyl)phenyl]-N-hydroxyacetamide,
[2-(4-pyridin-2-yl-piperazine-1-sulfonyl)phenyl]-N-hydroxyacetamide,
2-{2-[4-(3,5-dichlorophenyl)piperazine-1-sulfonyl]phenyl}-N-hydroxyacetamide,
{2-[4-(4-chlorophenoxy)piperidine-1-sulfonyl]phenyl}-N-hydroxyacetamide,
[2-(4-benzoylpiperidine-1-sulfonyl)phenyl]-N-hydroxyacetamide,
[2-(3,4-dihydro-1H-isoquinoline-2-sulfonyl)phenyl]-N-hydroxyacetamide, and
{2-[(4-methoxyphenyl)methyl-sulfamoyl]phenyl}-N-hydroxyacetamide.

13. A compound selected from the group consisting of

N-hydroxy-2-[(4-methoxyphenyl)methylsulfamoyl]benzamide,
N-hydroxy-2-[4-(pyridin-2-yl)piperazine-1-sulfonyl]benzamide,
2-(3,4-dihydro-1H-isoquinoline-2-sulfonyl)-N-hydroxybenzamide,
2-[4-(4-chlorophenoxy)piperidine-1-sulphonylmethyl]-N-hydroxybenzamide,
2-[4-(4-chlorobenzoyl)piperidine-1-sulfonylmethyl]-N-hydroxybenzamide,
2-(3,4-dihydro-1H-isoquinoline-2-sulfonylmethyl)-N-hydroxybenzamide,
2-[(benzofuran-2-ylmethyl-methyl-sulfamoyl)methyl]-N-hydroxybenzamide,
N-hydroxy-2-[4-(5-trifluromethylpyridin-2-yl)piperazine-1-sulfonylmethyl]benzamide,
2-{4-[4-(1,1-difluoromethoxy)phenyl]piperazine-1-sulphonylmethyl}-N-hydroxybenzamide,
N-hydroxy-2-{[(4-methoxyphenyl)methyl-sulfamoyl]methyl}benzamide,
2-{2-[4-(4-difluoromethoxyphenyl)piperazine-1-sulfonyl]phenyl}-N-hydroxyacetamide,
N-hydroxy-2-{2-[4-(5-trifluoromethylpyridin-2-yl)piperazine-1-sulfonyl]phenyl}acetamide,
2-{4,5-dimethoxy-2-[4-(5-trifluoromethylpyridin-2-yl)-piperazine-1-sulfonyl]phenyl}-N-hydroxyacetamide,
2-{2-[4-(4-chlorophenyl)piperazine-1-sulfonyl]phenyl}-N-hydroxy-3-methylbutyramide,
2-(2-{4-[(4-chlorophenyl)hydroxyiminomethyl]piperidine-1-sulfonyl}phenyl)-N-hydroxyacetamide, and
3-[4-(4-chlorophenyl)piperazine-1-sulfonyl]-N-hydroxybenzamide.

14. A pharmaceutical composition for use in therapy, comprising a compound of claim 1, and a pharmaceutically-acceptable diluent or carrier.

* * * * *